(12) United States Patent
Lucas et al.

(10) Patent No.: US 8,410,104 B2
(45) Date of Patent: *Apr. 2, 2013

(54) PYRIDAZINES

(75) Inventors: Matthew C. Lucas, Verona, NJ (US); Andrew Thomas, Binningen (CH)

(73) Assignees: Hoffmann-La Roche Inc., Nutley, NJ (US); Roche Palo Alto LLC, Palo Alto, CA (US)

( * ) Notice: Subject to any disclaimer, the term of this patent is extended or adjusted under 35 U.S.C. 154(b) by 253 days.

This patent is subject to a terminal disclaimer.

(21) Appl. No.: 12/768,765

(22) Filed: Apr. 28, 2010

(65) Prior Publication Data

US 2010/0286159 A1 Nov. 11, 2010

(30) Foreign Application Priority Data

May 5, 2009 (EP) .................................. 09159412

(51) Int. Cl.
*A61K 31/501* (2006.01)
*C07D 413/12* (2006.01)
*C07D 413/14* (2006.01)

(52) U.S. Cl. .................. 514/252.01; 544/238

(58) Field of Classification Search ........................ None
See application file for complete search history.

(56) References Cited

U.S. PATENT DOCUMENTS

| 4,639,266 | A | 1/1987 | Heubach et al. |
| 2003/0055085 | A1 | 3/2003 | Wagener et al. |
| 2004/0006226 | A1 | 1/2004 | Ladduwahetty et al. |
| 2010/0280019 | A1* | 11/2010 | Jakob-Roetne et al. ... 514/227.8 |
| 2010/0280020 | A1* | 11/2010 | Jakob-Roetne et al. ... 514/227.8 |

FOREIGN PATENT DOCUMENTS

| EP | 1894928 | 3/2008 |
| GB | 2336589 | 10/1999 |
| WO | 0129015 | 4/2001 |
| WO | 0134603 | 5/2001 |
| WO | 0250062 | 6/2002 |
| WO | 02081474 | 10/2002 |
| WO | 03004027 | 1/2003 |
| WO | 03015771 | 2/2003 |
| WO | 03044017 | 5/2003 |
| WO | 2004048349 | 6/2004 |
| WO | 2005014553 | 2/2005 |
| WO | 2005118568 | 12/2005 |
| WO | 2005123672 | 12/2005 |
| WO | 2006/018260 | 2/2006 |
| WO | 2006037480 | 4/2006 |
| WO | 2006044617 | 4/2006 |
| WO | 2006069155 | 6/2006 |
| WO | 2007039389 | 4/2007 |
| WO | 2007076260 | 7/2007 |
| WO | 2007092751 | 8/2007 |
| WO | 2008025539 | 3/2008 |
| WO | 2008025540 | 3/2008 |
| WO | 2009/071477 | 6/2009 |

OTHER PUBLICATIONS

McNamara et al., Psychobiology (1993), vol. 21, pp. 101-108.
Goodman et al., Tetrahedron (1999) vol. 55 pp. 15067-15070.
Abstract corresponding to JP 2007/230909, (2007).
Roy et al., Synthesis, 2003 pp. 1347-1356.
White, et al., Journal of Organic Chemistry (1981), vol. 46(11) pp. 2273-2280.
Shi Shun et al., J. Org. Chem. vol. 68 (2003) pp. 6810-6813.
Lam et al., Bioorganic & Medicinal Chemistry Letters (2003) vol. 13(10) pp. 1795-1799.
Wang et al., Journal of Fluorine Chemistry, vol. 111(2) pp. 241-246 (2001).
Hamper et al., J. Agric. Food Chem. (1995), vol. 43, pp. 219-228.
Kumar, et al., Tetrahedron Letters, vol. 47, (2006), p. 1457-1460.
Burke, et al., Journal of Natural Products, 1986, vol. 49, pp. 522-523.
Hormi, Organic Syntheses, vol. 8, p. 247 (1993) & vol. 66, (1988), p. 173.
Andosova et al., Pharmaceutical Chemistry Journal (English Translation), vol. 12, No. 8, 1978, pp. 1019-1022.
Doyle, et al., Journal of the Chem. Society, 1963, pp. 5838-5845.
Anderson, et al., Journal of Organic Chem. vol. 51(6), 1986, pp. 945-947.
Bourbeau et al., Organic Letters, vol. 8(17), 2006, pp. 3679-3680.
Waldo et al., Org. Lett. vol. (7) pp. 5203-5205 (2005).
Seydel et al., J. Med. Chem. vol. (19) pp. 483-492 (1976).
Kirk, K. L., J. Org. Chem. vol. (43) pp. 4381-4383 (1978).
Hüttel et al., Liebigs, Ann. Chem. vol. 593, pp. 200-207 (1955) (English translation).
Austin et al., J. Org. Chem. vol. 46, pp. 2280-2286 (1981).
Schlosser et al., Eur. J. Org. Chem. vol. (24), p. 4181-4184 (2002).
Félix et al., J. Org. Chem. 1995, vol. 60 p. 3907-3909.
Otani et al., Neuroscience Letters, 2005, vol. 381 pp. 108-113.
Papadimitriou et al., Neuropsychobiology, 2001, vol. 43(3) pp. 141-144.
McCauley et al., American J. Med. Genetics, 2004, 131B, pp. 51-59.
Delong et al., Autism, 2007, vol. 11(2) pp. 135-147.
Solis Anez et al., Investigacion Clinica, 2007 vol. 28, pp. 529-541.
Fernandez et al., Nature, Neuroscience, 2007, vol. 10 pp. 411-413.
Rueda et al., Neuroscience Letters, 2008, vol. 433 pp. 22-27.
Cui et al., Cell. 2008, vol. 135, pp. 549-560.
Deshayes et al., Synthesis, 1984, pp. 868-870.
Bromidge S M et al, Bioorganic & Medicinal Chemistry Letters, 10:16 (2000) 1867-1870 XP004216018.
International Search Report by EPO for Case 25374 WO, International Appl No. PCT?EP2010/055669, mailed Aug. 3, 2010.

* cited by examiner

*Primary Examiner* — Emily Bernhardt
(74) *Attorney, Agent, or Firm* — George W. Johnston; Patricia S. Rocha-Tramaloni; Kimberly J. Prior

(57) ABSTRACT

The present invention is concerned with isoxazole-pyridazines of formula I, having affinity and selectivity for GABA A α5 receptor, their manufacture, pharmaceutical compositions containing them and their use as therapeutically active substances. The active compounds of the present invention are useful as cognitive enhancer or for the therapeutic and/or prophylactic treatment of cognitive disorders like Alzheimer's disease.

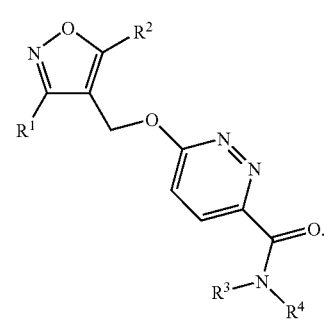

I

13 Claims, No Drawings

PYRIDAZINES

PRIORITY TO RELATED APPLICATION(S)

This application claims the benefit of European Patent Application No. 09159412.7, filed May 5, 2009, which is hereby incorporated by reference in its entirety.

FIELD OF THE INVENTION

The present invention is concerned with isoxazole-pyridazines having affinity and selectivity for GABA A α5 receptor, their manufacture, pharmaceutical compositions containing them and their use as therapeutically active substances.

BACKGROUND OF THE INVENTION

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex which is a membrane-bound heteropentameric protein polymer is composed principally of α, β and γ subunits.

Presently a total number of 21 subunits of the GABA A receptor have been cloned and sequenced. Three types of subunits (α, β and γ) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the α and γ subunits. Among the recombinant GABA A receptors, α1β2γ2 mimics many effects of the classical type-I BzR subtypes, whereas α2β2γ2, α3β2γ2 and α5β2γ2 ion channels are termed type-II BzR.

It has been shown by McNamara and Skelton in Psychobiology, 1993, 21:101-108 that the benzodiazepine receptor inverse agonist β-CCM enhance spatial learning in the Morris watermaze. However, β-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A α5 receptor partial or full inverse agonist which is relatively free of activity at GABA A α1 and/or α2 and/or α3 receptor can be used to provide a therapeutically active substance which is useful for enhancing cognition with reduced or without proconvulsant activity. It is also possible to use GABA A α5 inverse agonists which are not free of activity at GABA A α1 and/or α2 and/or α3 receptor but which are functionally selective for α5 containing subunits. However, inverse agonists which are selective for GABA A α5 subunits and are relatively free of activity at GABA A α1, α2 and α3 receptor are preferred.

Literature has been published to establish the link between GABA A α5 subunits and the therapeutic and/or prophylactic treatment of various diseases of the Central Nervous System, like Neuroscience Letts., 2005, 381, 108-13, Neuropsychobiology, 2001, 43(3), 141-44, Amer. J. Med. Genetics, 2004, 131B, 51-9, Autism 2007, 11(2): 135-47, Investigacion Clinica, 2007, 48, 529-41, Nature Neuroscience, 2007, 10, 411-13, Neuroscience Letts., 2008, 433, 22-7 and Cell 2008, 135, 549-60.

SUMMARY OF THE INVENTION

In particular, the present invention provides isoxazole-pyridazines of formula I.

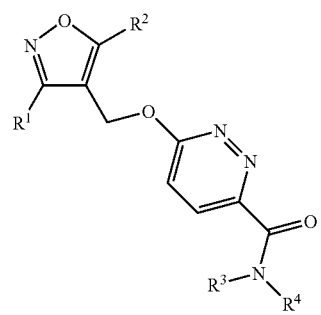

wherein
$R^1$ is lower alkyl or lower alkyl substituted by 1-5 substituents individually selected from amino, halogen, (lower alkyl, lower alkyl)N— and (lower alkyl, H)N—;
$R^2$ is H, lower alkyl or lower alkyl substituted by 1-5 substituents individually selected from amino, halogen, halogen-lower alkoxy, hydroxy, lower alkoxy, (lower alkyl, lower alkyl)N—, (lower alkyl, H)N—, nitro and lower alkyl-$S(O)_2$—;
$R^3$ is H, lower alkyl or lower alkyl substituted by 1-5 substituents individually selected from amino, halogen, halogen-lower alkoxy, hydroxy, lower alkoxy, (lower alkyl, lower alkyl)N—, (lower alkyl, H)N—, nitro and lower alkyl-$S(O)_2$—;
$R^4$ is selected from the group consisting of
  i) H,
  ii) lower alkyl,
  iii) lower alkyl substituted by 1-5 substituents individually selected from amino, halogen, halogen-lower alkoxy, hydroxy, lower alkoxy, (lower alkyl, lower alkyl)N—, (lower alkyl, H)N—, nitro and lower alkyl-$S(O)_2$—;
  iv) heterocyclyl, and
  v) heterocyclyl substituted by 1-4 substituents individually selected from amino, halogen, halogen-lower alkoxy, halogen-lower alkyl, hydroxy, hydroxy-lower alkyl, lower alkoxy, lower alkoxy-lower alkyl, lower alkyl, (lower alkyl, lower alkyl)N—, (lower alkyl, H)N—, nitro and lower alkyl-$S(O)_2$—;
or pharmaceutically acceptable salts or esters thereof.

DETAILED DESCRIPTION OF THE INVENTION

The present invention provides compounds of formula I and their pharmaceutically acceptable salts and esters and pharmaceutical compositions containing them. The invention also provides methods for the preparation of the above mentioned compounds and compositions. Further, the invention provides methods for the treatment or prevention of diseases related to the GABA A α5 receptor. The compounds of present invention are preferably inverse agonists of GABA A α5.

The compounds of present invention and their pharmaceutically acceptable salts and esters can be used, alone or in combination with other drugs, as cognitive enhancers or for the treatment or prevention of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders.

The following definitions of the general terms used in the present description apply irrespective of whether the terms in question appear alone or in combination.

The term "lower alkyl", alone or in combination with other groups, stands for a hydrocarbon radical which is linear or branched, with single or multiple branching, whereby the alkyl group in comprises 1 to 6 carbon atoms, for example, methyl (Me), ethyl (Et), propyl, isopropyl (i-propyl), n-butyl, i-butyl (iso-butyl), 2-butyl (sec-butyl), t-butyl (tert-butyl) and the like. Preferred alkyl groups are groups with 1 to 4 carbon atoms. Most preferred are methyl, ethyl, isopropyl, propyl and n-butyl.

The phrase "lower alkyl substituted by", alone or in combination with other groups, refers to lower alkyl, which is substituted by one or multiple substituents, preferably 1-5 substituents, individually selected from the group consisting of acetamidyl, acetyl, acetylamino, amido, amino, carboxy, cyano, cycloalkyl, halogen, halogen-lower alkoxy, halogen-lower alkyl, heterocyclyl, hydroxy, hydroxy-lower alkyl, lower alkoxy, lower alkoxy-lower alkyl, (lower alkyl, lower alkyl)N—, (lower alkyl, H)N—, nitro, lower alkyl-S(O)$_2$— and the like. Preferred substituent is hydroxy. Preferred substituted lower alkyl are hydroxy-lower alkyl. Most preferred are 2-hydroxy-1-methyl-ethyl, 2-hydroxy-2-methyl-propyl.

The term "halogen", alone or in combination with other groups, denotes chlorine (Cl), iodine (I), fluorine (F) and bromine (Br).

The term "heterocyclyl", alone or in combination with other groups, refers to a 4 to 8 membered ring containing 1, 2 or 3 ring heteroatoms individually selected from N, O and S, with 1 or 2 ring heteroatoms are preferred. The heterocyclyl can be part of a bicyclic spiro ring. Preferred are 4 to 6 membered heterocyclyl, more preferred 5 to 6 membered heterocyclyl, each containing 1 or 2 ring heteroatoms selected from N, O and S. Examples of such heterocyclyl groups include pyrrolidinyl (pyrrolidinyl), tetrahydrofuranyl (tetrahydrofuryl), tetrahydrothienyl, tetrahydropyridyl (tetrahydropyridinyl), tetrahydropyranyl (tetrahydropyryl), azetidyl (azetidinyl), thiazolidyl (thiazolidinyl), oxazolidyl (oxazolidinyl), piperidyl (piperidinyl), morpholinyl, thiomorpholinyl, piperazinyl, azepanyl, diazepanyl, oxazepanyl and the like. Preferred heterocyclyl groups are tetrahydrofuryl and tetrahydropyryl.

The phrase "heterocyclyl substituted by", alone or in combination with other groups, refer to a heterocyclyl, which is substituted by one or multiple substituents, preferably 1-4 substituents, whereby substitution at each ring atom individually is possible, with a substituent individually selected from the group consisting of amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl, lower alkyl)N—, (lower alkyl, H)N—, N(lower alkyl, lower alkyl)-lower alkyl, N(lower alkyl, H)-lower alkyl, nitro, lower alkyl-S(O)$_2$—, carboxy, carboxy-lower alkyl, lower alkyl-COO-lower alkyl, lower alkyl-COO—, CO—N(lower alkyl, H)-lower alkyl, CO—N(lower alkyl, lower alkyl)-lower alkyl, CO—NH$_2$-lower alkyl, lower alkyl-CO— and the like.

The term "lower alkoxy", alone or in combination with other groups, stands for a "—O-lower alkyl" radical which can be linear or branched, with single or multiple branching, whereby the alkyl group in comprises 1 to 6 carbon atoms, for example, methoxy (OMe, MeO), ethoxy (OEt), propoxy, isopropoxy (i-propoxy), n-butoxy, i-butoxy (iso-butoxy), 2-butoxy (sec-butoxy), t-butoxy (tert-butoxy), isopentyloxy (i-pentyloxy) and the like. Preferred alkoxy groups are groups with 1 to 4 carbon atoms.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable salts" refers to salts that are suitable for use in contact with the tissues of humans and lower animals without undue toxicity, irritation, allergic response, and the like, and are commensurate with a reasonable benefit-risk ratio. Examples of suitable salts with inorganic and organic acids are, but are not limited to, hydrochloric acid, nitric acid, sulfuric acid, phosphoric acid, sulphuric acid, citric acid, formic acid, fumaric acid, maleic acid, lactic acid, malic acid, acetic acid, succinic acid, tartaric acid, methane-sulfonic acid, p-toluenesulphonic acid, trifluoroacetic acid and the like.

The term "pharmaceutically acceptable esters" refers to a conventionally esterified compound having a carboxyl group. Examples of ester groups which are cleaved (in this case hydrolyzed) in vivo to the corresponding carboxylic acids are those in which the cleaved hydrogen is replaced with—lower alkyl which is optionally substituted with heterocyclyl, cycloalkyl, etc. Examples of substituted lower alkyl esters are those in which—lower alkyl is substituted with pyrrolidine, piperidine, morpholine, N-methylpiperazine, etc. Furthermore, the term "pharmaceutically acceptable esters" refers to a conventionally esterified compound having a hydroxy group. The hydroxy compounds can be converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which acids are non-toxic to living organisms.

The terms "pharmaceutically acceptable carrier" and "pharmaceutically acceptable auxiliary substance" refer to carriers and auxiliary substances such as diluents or excipients that are compatible with the other ingredients of the formulation and not deleterious to the recipient thereof.

"Therapeutically effective amount" means an amount that is effective to prevent, alleviate or ameliorate symptoms of disease or prolong the survival of the subject being treated.

The compounds of formula I can contain one or more asymmetric centres and can therefore occur as racemates, racemic mixtures, single enantiomers, diastereomeric mixtures and individual diastereomers. Additional asymmetric centres can be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to comprehend all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric centre of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

Substituents at a double bond or a ring can be present in cis (=Z—) or trans (=E-) form, unless the stereochemistry is explicitly depicted in the corresponding compound formula I.

The term "pharmaceutical composition" encompasses a product comprising specified ingredients in pre-determined amounts or proportions, as well as any product that results, directly or indirectly, from combining specified ingredients in specified amounts. Preferably it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The following table lists abbreviations used within the present document.

TABLE 1

| abbreviations | |
|---|---|
| CDI | 1,1'-carbonyldiimidazole |
| DCM | dichloromethane |
| DIPEA | N,N-diisopropylethylamine (Hunig's Base) |
| DMAP | N,N-dimethylamino-4-pyridine |
| DMF | N,N-dimethylformamide |
| DMSO | dimethylsulfoxide |
| DPPF | 1,1'-bis(diphenylphosphino)ferrocene |
| EDAC | 1-ethyl-3-(3-dimethylaminopropyl) carbodiimide hydrochloride |
| h | hour(s) |
| HOBt | N-1-hydroxybenzotriazole |
| LiOH, NaOH | lithium hydroxide, sodium hydroxide |
| $Me_3Al$ | trimethylaluminium |
| MeOH, EtOH | methanol, ethanol |
| MS | mass spectrum |
| $Na_2CO_3$ | sodium carbonate |
| NADP | nicotinamide adenine dinucleotide phosphate |
| NaH | sodium hydride |
| on | overnight |
| $Pd(OAc)_2$ | palladium acetate |
| rt | room temperature |
| Seignette's salt | potassium sodium tartrate |
| TBD | 1,5,7-triazabicyclo[4.4.0]dec-5-ene |
| TBDMS | tert-butyldimethylsilyl |
| TBTU | O-(benzotriazol-1-yl)-N,N,N',N'-tetramethyluronium tetrafluoroborate |
| THF | tetrahydrofuran |

The invention also provides pharmaceutical compositions, methods of using, and methods of preparing the aforementioned compounds.

While the present invention has been described with reference to the specific embodiments thereof, it should be understood by those skilled in the art that various changes can be made and equivalents can be substituted without departing from the true spirit and scope of the invention. In addition, many modifications can be made to adapt a particular situation, material, composition of matter, process, process step or steps, to the objective spirit and scope of the present invention. All such modifications are intended to be within the scope of the claims appended hereto. All separate embodiments can be combined.

The invention therefore also relates to pharmaceutical compositions comprising a compound as defined herewithin and a pharmaceutically acceptable carrier and/or adjuvant.

One embodiment of the invention is compounds of formula I,

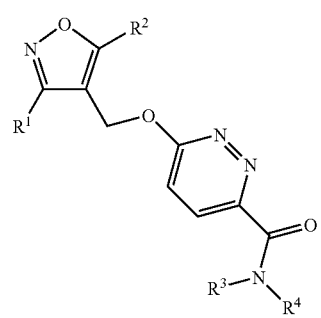

wherein
$R^1$ is lower alkyl or lower alkyl substituted by 1-5 substituents individually selected from amino, halogen, (lower alkyl, lower alkyl)N— and (lower alkyl, H)N—;
$R^2$ is H, lower alkyl or lower alkyl substituted by 1-5 substituents individually selected from amino, halogen, halogen-lower alkoxy, hydroxy, lower alkoxy, (lower alkyl, lower alkyl)N—, (lower alkyl, H)N—, nitro and lower alkyl-S$(O)_2$—;
$R^3$ is H, lower alkyl or lower alkyl substituted by 1-5 substituents individually selected from amino, halogen, halogen-lower alkoxy, hydroxy, lower alkoxy, (lower alkyl, lower alkyl)N—, (lower alkyl, H)N—, nitro and lower alkyl-S$(O)_2$—;
$R^4$ is selected from the group consisting of
  i) H,
  ii) lower alkyl,
  iii) lower alkyl substituted by 1-5 substituents individually selected from amino, halogen, halogen-lower alkoxy, hydroxy, lower alkoxy, (lower alkyl, lower alkyl)N—, (lower alkyl, H)N—, nitro and lower alkyl-S$(O)_2$—,
  iv) heterocyclyl, and
  v) heterocyclyl substituted by 1-4 substituents individually selected from amino, halogen, halogen-lower alkoxy, halogen-lower alkyl, hydroxy, hydroxy-lower alkyl, lower alkoxy, lower alkoxy-lower alkyl, lower alkyl, (lower alkyl, lower alkyl)N—, (lower alkyl, H)N—, nitro and lower alkyl-S$(O)_2$—;
or pharmaceutically acceptable salts or esters thereof.

One certain embodiment of the invention is compounds, wherein $R^1$ is lower alkyl.

One certain embodiment of the invention is compounds, wherein $R^1$ is n-butyl.

One certain embodiment of the invention is compounds, wherein $R^2$ is lower alkyl.

One certain embodiment of the invention is compounds, wherein $R^2$ is methyl.

One certain embodiment of the invention is compounds, wherein $R^3$ is H.

One certain embodiment of the invention is compounds, wherein $R^4$ is selected from i) H,
ii) lower alkyl,
iii) lower alkyl substituted by 1-2 hydroxy groups, and
iv) heterocyclyl.

One certain embodiment of the invention is compounds, wherein $R^4$ is selected from
i) lower alkyl,
ii) lower alkyl substituted by 1-2 hydroxy groups, and
iii) heterocyclyl.

One certain embodiment of the invention is compounds, wherein $R^4$ is individually selected from lower alkyl, lower alkyl substituted by 1-2 hydroxy groups and heterocyclyl.

One certain embodiment of the invention is compounds, wherein $R^4$ is H.

One certain embodiment of the invention is compounds, wherein $R^4$ is lower alkyl.

One certain embodiment of the invention is compounds, wherein $R^4$ is isopropyl.

One certain embodiment of the invention is compounds, wherein $R^4$ is lower alkyl substituted by 1-2 hydroxy groups.

One certain embodiment of the invention is compounds, wherein $R^4$ is 2-hydroxy-1-methyl-ethyl.

One certain embodiment of the invention is compounds, wherein $R^4$ is 2-hydroxy-2-methyl-propyl.

One certain embodiment of the invention is compounds, wherein $R^4$ is heterocyclyl.

One certain embodiment of the invention is compounds, wherein $R^4$ is tetrahydropyranyl.

One certain embodiment of the invention is compounds, wherein $R^4$ is tetrahydrofuranyl.

One certain embodiment of the invention is compounds, wherein $R^4$ is H, isopropyl, tetrahydropyranyl, tetrahydrofuranyl, 2-hydroxy-1-methyl-ethyl or 2-hydroxy-2-methyl-propyl.

One certain embodiment of the invention is compounds, wherein $R^4$ is isopropyl, tetrahydrofuranyl, 2-hydroxy-1-methyl-ethyl or 2-hydroxy-2-methyl-propyl.

One certain embodiment of the invention is compounds individually selected from the group consisting of
6-(3-Butyl-5-methyl-isoxazol-4-ylmethoxy)-pyridazine-3-carboxylic acid isopropylamide,
6-(3-Butyl-5-methyl-isoxazol-4-ylmethoxy)-pyridazine-3-carboxylic acid (tetrahydro-pyran-4-yl)-amide,
6-(3-Butyl-5-methyl-isoxazol-4-ylmethoxy)-pyridazine-3-carboxylic acid ((R)-2-hydroxy-1-methyl-ethyl)-amide,
6-(3-Butyl-5-methyl-isoxazol-4-ylmethoxy)-pyridazine-3-carboxylic acid (2-hydroxy-2-methyl-propyl)-amide,
6-(3-Butyl-5-methyl-isoxazol-4-ylmethoxy)-pyridazine-3-carboxylic acid ((S)-2-hydroxy-1-methyl-ethyl)-amide,
(S)-6-(3-Butyl-5-methyl-isoxazol-4-ylmethoxy)-pyridazine-3-carboxylic acid (tetrahydrofuran-3-yl)-amide,
6-(3-Butyl-5-methyl-isoxazol-4-ylmethoxy)-pyridazine-3-carboxylic acid (2-hydroxy-1-methyl-ethyl)-amide,
6-(3-Butyl-5-methyl-isoxazol-4-ylmethoxy)-pyridazine-3-carboxylic acid (tetrahydrofuran-3-yl)-amide, and
6-(3-Butyl-5-methyl-isoxazol-4-ylmethoxy)-pyridazine-3-carboxylic acid amide,
or pharmaceutically acceptable salts or esters thereof.

One certain embodiment of the invention is compounds individually selected from the group consisting of
(S)-6-(3-Butyl-5-methyl-isoxazol-4-ylmethoxy)-pyridazine-3-carboxylic acid (tetrahydrofuran-3-yl)-amide,
6-(3-Butyl-5-methyl-isoxazol-4-ylmethoxy)-pyridazine-3-carboxylic acid isopropylamide,
6-(3-Butyl-5-methyl-isoxazol-4-ylmethoxy)-pyridazine-3-carboxylic acid ((R)-2-hydroxy-1-methyl-ethyl)-amide,
6-(3-Butyl-5-methyl-isoxazol-4-ylmethoxy)-pyridazine-3-carboxylic acid ((S)-2-hydroxy-1-methyl-ethyl)-amide, and
6-(3-Butyl-5-methyl-isoxazol-4-ylmethoxy)-pyridazine-3-carboxylic acid (2-hydroxy-1-methyl-ethyl)-amide,
or pharmaceutically acceptable salts or esters thereof.

One certain embodiment of the invention is (S)-6-(3-Butyl-5-methyl-isoxazol-4-ylmethoxy)-pyridazine-3-carboxylic acid (tetrahydro-furan-3-yl)-amide, or pharmaceutically acceptable salts or esters thereof.

One certain embodiment of the invention is a process for preparing a compound of formula I as defined herewithin, which process comprises reacting a compound of formula $R^3R^4NH$ (II) with a compound of formula III,

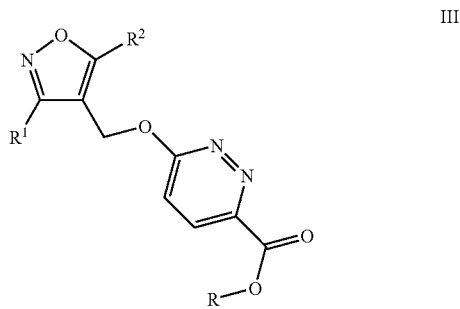

wherein any residues and variables have any of the meanings as defined herewithin and R is lower alkyl or H.

One certain embodiment of the invention is a compound as described herewithin, whenever prepared by a process as defined above.

One certain embodiment of the invention is a compound as described herewithin for the use as a therapeutically active substance.

One certain embodiment of the invention is a compound as described herewithin for the use as therapeutically active substance.

One certain embodiment of the invention is a compound as described herewithin for the use for the therapeutic and/or prophylactic treatment of a disorder or condition mediated by the GABA A α5 receptor, or that can be treated via modulation of the GABA A α5 receptor.

One certain embodiment of the invention is a compound as described herewithin for the use as therapeutically active substance for the treatment or prevention of diseases related to the GABA A α5 receptor.

One certain embodiment of the invention is a compound as described herewithin for the use for the therapeutic and/or prophylactic treatment of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

Specific indications using the compounds of the present invention are cognitive disorders, schizophrenia, positive, negative and/or cognitive symptoms associated with schizophrenia and Alzheimer's disease, particularly schizophrenia and Alzheimer's disease and more particularly Alzheimer's disease.

One certain embodiment of the invention is a therapeutically active substance, comprising a compound as described herewithin.

One certain embodiment of the invention is a pharmaceutical composition comprising a compound as described herewithin as an active ingredient and a pharmaceutically acceptable carrier and/or a pharmaceutically acceptable auxiliary substance.

One certain embodiment of the invention is a pharmaceutical composition, comprising a compound as described herewithin for the therapeutic and/or prophylactic treatment of a disorder or condition mediated by the GABA A α5 receptor, or that can be treated via modulation of the GABA A α5 receptor.

One certain embodiment of the invention is a pharmaceutical composition, comprising a compound as described herewithin for the manufacture of a medicament for the therapeutic and/or prophylactic treatment of diseases which are related to the GABA A α5 receptor.

One certain embodiment of the invention is a pharmaceutical composition, comprising a compound as described herewithin for the therapeutic and/or prophylactic treatment of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

One certain embodiment of the invention is the use of a compound as described herewithin for the manufacture of a medicament for the therapeutic and/or prophylactic treatment of a disorder or condition mediated by the GABA A α5 receptor, or that can be treated via modulation of the GABA A α5 receptor.

One certain embodiment of the invention is the use of a compound as described herewithin for the therapeutic and/or prophylactic treatment of a diseases which are related to the GABA A α5 receptor.

One certain embodiment of the invention is the use of a compound as described herewithin for the manufacture of a medicament for the therapeutic and/or prophylactic treatment of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

One certain embodiment of the invention is the use of a compound as described herewithin for the therapeutic and/or prophylactic treatment of a disorder or condition mediated by the GABA A α5 receptor, or that can be treated via modulation of the GABA A α5 receptor.

One certain embodiment of the invention is the use of a compound as described herewithin for the therapeutic and/or prophylactic treatment of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

One certain embodiment of the invention is a method for the therapeutic and/or prophylactic treatment of a disorder or condition mediated by the GABA A α5 receptor, or that can be treated via modulation of the GABA A α5 receptor, particularly for the therapeutic and/or prophylactic treatment of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers, which method comprises administering a compound as described herewithin to a mammal, particularly to a human being.

Reaction Schemes

The compounds of formula I can be prepared in accordance with the following schemes. The starting material is commercially available or can be prepared in accordance with known methods. Any previously defined residues and variables will continue to have the previously defined meaning unless otherwise indicated.

The present compounds of formula I and their pharmaceutically acceptable salts can be prepared by a process comprising the steps of:

A) Reacting a compound of formula 1 with hydroxylamine hydrochloride in a suitable solvent, such as ethanol and water in the presence of a base, such as aqueous sodium hydroxide to give a compound of formula 2, followed by reacting the compound of formula 2 with a chlorinating agent such as N-chlorosuccinimide in a suitable solvent, such as DMF to give a compound of formula 3.

Scheme 1: Synthesis of intermediates 3

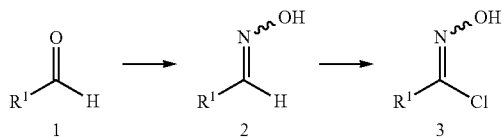

B) A compound of formula 3 is then further reacted to a compound of formula 7 by reacting
i) with a compound of formula 4 in the presence of a suitable base, such as triethylamine, in a suitable solvent, such as chloroform, or
ii) with a compound of formula 5 in the presence of a suitable base, such as triethylamine, in a suitable solvent, such as diethylether, or
iii) with a compound of formula 6 in the presence of a suitable base, such as triethylamine, in a suitable solvent, such as diethylether.

Scheme 2: Synthesis of intermediates 7

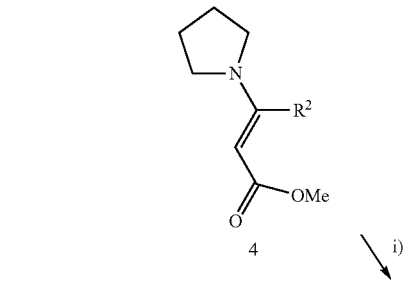

C) A compound of formula 7 is then reacted to a compound of formula 9 with
i) a reducing agent, such as lithiumaluminiumhydride, in a suitable solvent, such as THF to give a compound of formula 9, or
ii-1) a hydrolytic agent such as NaOH or LiOH in a suitable solvent such as THF, MeOH or EtOH, water to give a compound of formula 8,
ii-2) followed by reacting a compound of formula 8 with a reducing agent, such as lithiumaluminiumhydride or ethyl chloroformate in the presence of sodiumborohydride in a suitable solvent such as THF or water.

Scheme 3: Synthesis of intermediates 9

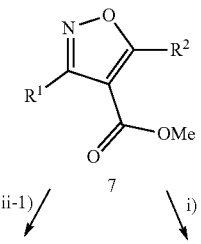

D) A compound of formula 9 is then reacted with compounds of formula 10 in the presence of a suitable base, such as sodium hydride, in a suitable solvent, such as THF, or to give a compound of formula 11.

Scheme 4: Synthesis of intermediates 11, with Y = Cl or I

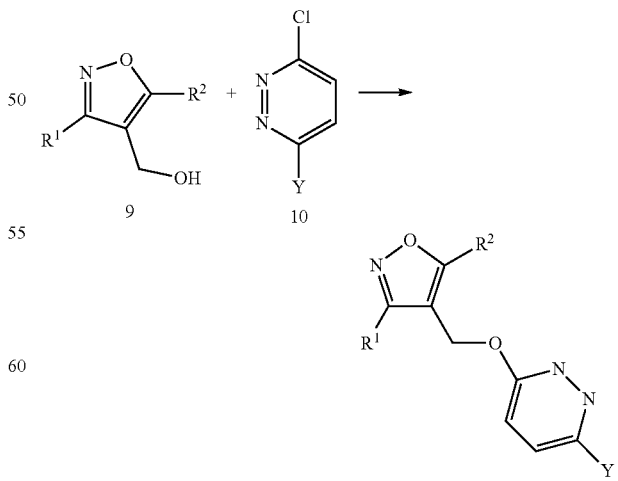

D) A compound of formula 11 is then reacted with a compound of formula 12 via standard alkoxycarbonylation method.

Scheme 5:
Synthesis of intermediates 11, with Y = Cl or I and R' = lower alkyl

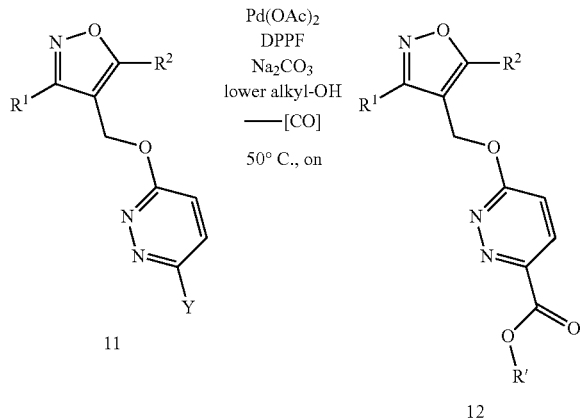

E) A compound of formula 12 can
i-1) be treated with a suitable base such as sodium hydroxide or lithium hydroxide in a suitable solvent, such as dioxane, water, THF or methanol to give a compound of formula 13, and i-2) react with a compound of formula II to a compound of formula I under conditions as described in the examples or under conditions well known to the person skilled in the art, e.g. the reaction can be performed in the presence of Hünigs Base (N,N-diisopropylethylamine) and O-(benzotriazol-1-yl)-N,N,N',N'-tetramethyluronium tetrafluoroborate in a suitable solvent like dimethylformamide at room temperature, or the reaction can be performed in the presence of 1,1'-carbonyldiimidazole in a suitable solvent like dimethylformamide at elevated temperatures e.g. at 80° C., or the reaction can be performed in the presence of 1-ethyl-3-(3-dimethylaminopropyl)carbodiimide hydrochloride, N1-hydroxybenzotriazole and Hünigs Base (N,N-diisopropylethylamine) in a suitable solvent like dichloromethane at room temperature, or ii) react with a compound of formula II directly to a compound of formula I under conditions as described in the examples or under conditions well known to the person skilled in the art, e.g. the reaction can be performed in the presence of trimethylaluminium in a suitable solvent like dioxane at elevated temperatures e.g. at 85-95° C. or the reaction can be performed in the presence of 1,5,7-triazabicyclo[4.4.0]dec-5-ene in a suitable solvent like toluene at elevated temperatures e.g. at 50° C.

Scheme 6: Synthesis of compounds of formula I, with R' = lower alkyl

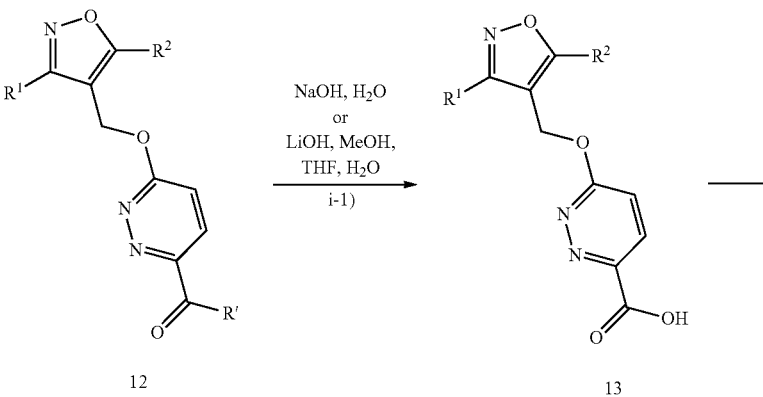

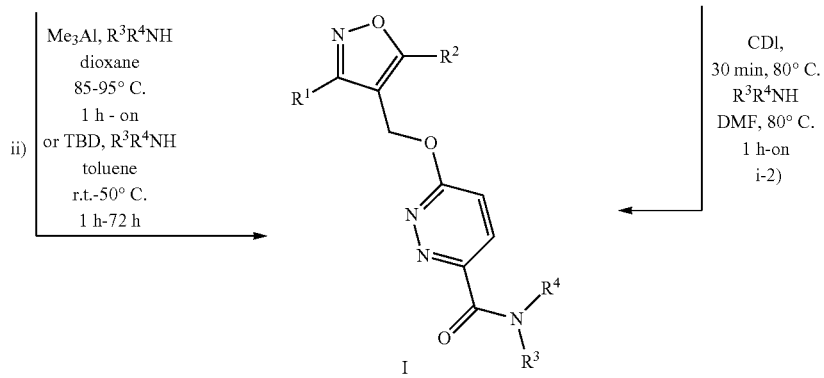

The corresponding salts with pharmaceutically acceptable acids can be obtained by standard methods known to the person skilled in the art, e.g. by dissolving the compound of formula I in a suitable solvent such as e.g. dioxane or THF and adding an appropriate amount of the corresponding pharmaceutically acceptable acid. The products can usually be isolated by filtration or by chromatography.

The conversion into pharmaceutically acceptable esters of compounds of formula I bearing a hydroxy group can be carried out e.g. by treatment of a suitable hydroxy group with a suitable alcohol using e.g. a condensating reagent such as benzotriazol-1-yloxytris(dimethylamino)-phosphonium hexafluorophosphate (BOP), N,N-dicylohexyl-carbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluoro-borate (TPTU), or by direct reaction with a suitable alcohol under acidic conditions, as for example in the presence of a strong mineral acid like hydrochloric acid, sulfuric acid and the like.

Insofar as their preparation is not described in the examples, the compounds of formula I as well as all intermediate products can be prepared according to analogous methods or according to the methods set forth herewithin. Starting materials are commercially available, known in the art or can be prepared by methods known in the art or in analogy thereto.

It will be appreciated that the compounds of formula I in this invention can be derivatized at functional groups to provide derivatives which are capable of conversion back to the parent compound in vivo.

Pharmacological Tests

The compounds of formula I and their pharmaceutically acceptable salts and esters possess valuable pharmacological properties. The compounds of the present invention are ligands for GABA A receptors containing the α5 subunit and are therefore useful in the therapy where cognition enhancement is required.

The compounds were investigated in accordance with the test given hereinafter:

Membrane Preparation and Binding Assay

The affinity of compounds at GABA A receptor subtypes was measured by competition for [$^3$H]flumazenil (85 Ci/mmol; Roche) binding to HEK293 cells expressing rat (stably transfected) or human (transiently transfected) receptors of composition α1β3γ2, α2β3γ2, α3β3γ2 and α5β3γ2.

Cell pellets were suspended in Krebs-tris buffer (4.8 mM KCl, 1.2 mM $CaCl_2$, 1.2 mM $MgCl_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were re-suspended in Krebs-tris buffer and homogenized by polytron for ca. 15 sec on ice. Protein was measured (Bradford method, Bio-Rad) and aliquots of 1 mL were prepared and stored at −80° C.

Radioligand binding assays were carried out in a volume of 200 mL (96-well plates) which contained 100 mL of cell membranes, [$^3$H]flumazenil at a concentration of 1 nM for α1, α2 and α3 subunits and 0.5 nM for α5 subunits and the test compound in the range of $10$-$10^{-3} \times 10^{-6}$ M. Nonspecific binding was defined by $10^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. Ki values were calculated using Excel-Fit (Microsoft) and are the means of two determinations.

The compounds of the accompanying examples were tested in the above described assay, and the preferred compounds were found to possess a Ki value for displacement of [$^3$H]flumazenil from α5 subunits of the rat GABA A receptor of 100 nM or less. Most preferred are compounds with a Ki (nM)<35. In a preferred embodiment the compounds of the invention are binding selective for the α5 subunit relative to the α1, α2 and α3 subunit. Representative test results are listed below.

TABLE 2 human Ki (hKi) values

| Ex. | hKi GABA A α5 (nM) |
|---|---|
| 1 | 12.8 |
| 2 | 16.6 |
| 3 | 7 |
| 4 | 17.3 |
| 5 | 17.3 |
| 6 | 8.6 |
| 7 | 10.4 |
| 8 | 6.9 |
| 9 | 7.3 |

Pharmaceutical Compositions

The invention also provides pharmaceutical compositions containing compounds of formula I as well as their pharmaceutically acceptable salts and esters and a pharmaceutically acceptable carrier. The pharmaceutical compositions of the invention can be formulated for any route of administration, such as oral, sub-lingual, buccal, parenteral (subcutaneous, intramuscular, intravenous), rectal, topical, intranasal and trough inhalation or insufflation, and comprise at least one compound of formula I or pharmaceutically acceptable salts or esters thereof, with any pharmaceutically suitable ingredient, excipient, carrier, adjuvant or vehicle. Oral pharmaceutical compositions are e.g. tablets, coated tablets, dragées, hard gelatin capsules, soft gelatin capsules, solutions, emulsions or suspensions. Rectal pharmaceutical compositions are e.g. in the form of suppositories.

The compounds of formula I and their pharmaceutically acceptable salts and esters can be processed with pharmaceutically inert, inorganic or organic excipients for the production of tablets, coated tablets, dragées and hard gelatin capsules. Examples are lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semisolid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

The pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of formula I or of the corresponding amount of a pharmaceutically acceptable salt or ester thereof. The daily dosage can be administered as single dose or in divided doses and, in addition, the upper limit can also be exceeded when necessary.

Examples of compositions according to the invention are, but are not limited to:

Example A

Tablets of the following composition are manufactured in the usual manner:

TABLE 3

| possible tablet composition | |
|---|---|
| ingredient | mg/tablet |
| Compound of formula I | 5 |
| Lactose | 45 |
| Corn starch | 15 |
| Microcrystalline cellulose | 34 |
| Magnesium stearate | 1 |
| Tablet weight | 100 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Example B

Capsules of the following composition are manufactured:

TABLE 4

| possible capsule composition | |
|---|---|
| ingredient | mg/capsule |
| Compound of formula I | 10 |
| Lactose | 155 |
| Corn starch | 30 |
| Talc | 5 |
| Capsule fill weight | 200 |

Manufacturing Procedure
1. Mix items 1, 2 and 3 in a suitable mixer for 30 minutes.
2. Add item 4 and mix for 3 minutes.
3. Fill into a suitable capsule.

The compound of formula I, lactose and corn starch are firstly mixed in a mixer and then in a comminuting machine. The mixture is returned to the mixer, the talc is added thereto and mixed thoroughly. The mixture is filled by machine into hard gelatin capsules.

Example C

Suppositories of the following composition are manufactured:

TABLE 5

| possible suppository composition | |
|---|---|
| ingredient | mg/supp. |
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool, the suppositories are then removed from the moulds and packed individually in wax paper or metal foil.

EXPERIMENTAL PART

The following examples 1-9 are provided for illustration of the invention. They should not be considered as limiting the scope of the invention, but merely as being representative thereof.

Example 1

6-(3-Butyl-5-methyl-isoxazol-4-ylmethoxy)-pyridazine-3-carboxylic acid isopropylamide

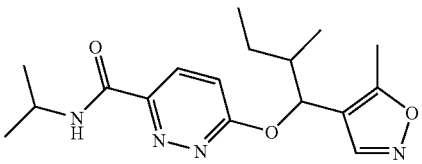 [SMILES: CCC(C)C(Oc1ccc(C(=O)NC(C)C)nn1)c1cnoc1C]

a) 3-Butyl-5-methyl-isoxazole-4-carboxylic acid ethyl ester

To a suspension of N-chlorosuccinimide (16.1 g, 121 mmol) in chloroform (250 mL) at room temperature was added pyridine (0.95 g, 12.0 mmol) then a solution of pentanal oxime (12.2 g, 121 mmol) in chloroform (250 mL) was added dropwise over 20 min. The reaction mixture was stirred at 50° C. for 2 h then cooled to room temperature and a solution of ethyl (E)-3-(1-pyrrolidino)-2-butenoate (22.1 g, 121 mmol) in chloroform (120 mL) added dropwise. The reaction mixture was warmed to 50° C. and a solution of triethylamine (12.2 g, 121 mmol) in chloroform (120 mL) added dropwise. After 15 h the reaction mixture was cooled and extracted with water then citric acid (10% w/w aqueous solution). The combined aqueous phases were extracted with dichloromethane, and the combined organic phases were dried, filtered and concentrated. Purification by chromatography (silica, heptane:ethyl acetate=100:0 to 9:1) afforded the title compound (10.9 g, 43%) as a pale yellow liquid. MS: m/e=232.2 [M+H]$^+$.

b) (3-Butyl-5-methyl-isoxazol-4-yl)-methanol

To a stirred solution of 3-butyl-5-methyl-isoxazole-4-carboxylic acid ethyl ester (9.8 g, 46.3 mmol) in THF (100 mL) under argon and at 0° C. was added lithiumaluminiumhydride (2.03 g, 53.4 mmol) in five portions. After 1 h the reaction mixture was quenched dropwise with Seignette salt solution. The reaction mixture was filtered and the filtrate extracted with ethyl acetate. The combined organic extracts were washed with Seignette salt solution then dried, filtered and concentrated. Purification by chromatography (silica, heptane:ethyl acetate=100:0 to 4:6) afforded the title compound (7.5 g, 95%) as a yellow liquid. MS: m/e=170.3 [M+H]$^+$.

c) 3-(3-Butyl-5-methyl-isoxazol-4-ylmethoxy)-6-chloro-pyridazine and 3-(3-butyl-5-methyl-isoxazol-4-ylmethoxy)-6-iodo-pyridazine To a stirred suspension of NaH (425 mg of a 55% dispersion in mineral oil) in THF (5 mL) at 0° C. under argon, was added a solution of (3-butyl-5-methyl-isoxazol-4-yl)-methanol (1.5 g, 8.9 mmol) in THF (5 mL) dropwise. The reaction mixture was warmed to room temperature. After 30 min the reaction mixture was cooled to 0° C. and a solution of 3-chloro-6-iodo-pyridazine (2.13 g, 8.9 mmol) in THF (5 mL) was added dropwise. After 2 h the reaction mixture was warmed to room temperature then quenched with water and extracted with ethyl acetate. The combined organic phases were dried, filtered and concentrated then purified by chromatography to give the title compounds (2.66 g) as a ~1:3 mixture and as a pale yellow liquid after purification by chromatography (silica, 0 to 60% ethyl acetate in heptane).

MS: m/e=282.2/374.2 [M+H]$^+$.

d) 6-(3-Butyl-5-methyl-isoxazol-4-ylmethoxy)-pyridazine-3-carboxylic acid methyl ester A suspension of 3-(3-butyl-5-methyl-isoxazol-4-ylmethoxy)-6-chloro-pyridazine and 3-(3-butyl-5-methyl-isoxazol-4-ylmethoxy)-6-iodo-pyridazine (~1:3 mixture, 2.6 g, ~7.0 mmol) and sodium carbonate (738 mg, 7.0 mmol) in methanol (20 mL) was evacuated and filled with argon five times. 1,1'-Bis(diphenylphosphino)ferrocene (386 mg, 0.7 mmol) and palladium(II) acetate (156 mg, 0.7 mmol) were added then the flask was evacuated again and filled with carbon monoxide. The reaction mixture was then heated to 50° C. After 15 h the reaction mixture was cooled, filtered through decalite and evaporated. The residue was purified by chromatography (silica, 0 to 50% ethyl acetate in heptane) to give the title compound (760 mg, ~36%) as an orange solid. MS: m/e=306.1 [M+H]$^+$.

e) 6-(3-Butyl-5-methyl-isoxazol-4-ylmethoxy)-pyridazine-3-carboxylic acid isopropylamide Trimethylaluminium (0.72 mL of a 2 M solution in toluene, 1.44 mmol) was added dropwise to a stirred solution of isopropylamine (85 mg, 1.44 mmol) in dioxane (3 mL) at room temperature under argon. After 1 h, a solution of 6-(3-butyl-5-methyl-isoxazol-4-ylmethoxy)-pyridazine-3-carboxylic acid methyl ester (110 mg, 0.36 mmol) in dioxane (3 mL) was added and the reaction mixture heated at 90° C. After 2 h the reaction mixture was cooled in an ice/water bath and quenched with Seignette salt solution (1 mL). The resultant mixture was filtered, the filter cake washed with dichloromethane, then the combined filtrates were concentrated then purified by chromatography (silica, 0 to 80% ethyl acetate in heptane) to give the title compound (45 mg, 38%) as a colourless oil. MS: m/e=333.4 [M+H]$^+$.

Example 2

6-(3-Butyl-5-methyl-isoxazol-4-ylmethoxy)-pyridazine-3-carboxylic acid (tetrahydro-pyran-4-yl)-amide

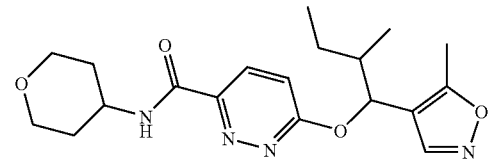 [SMILES: CCC(C)C(Oc1ccc(C(=O)NC2CCOCC2)nn1)c1cnoc1C]

As described for example 1e, 6-(3-butyl-5-methyl-isoxazol-4-ylmethoxy)-pyridazine-3-carboxylic acid methyl ester (110 mg, 0.36 mmol) was converted, using 4-aminotetrahydropyran instead of isopropylamine, to the title compound (100 mg, 74%) which was obtained as a colourless oil after purification by chromatography (silica, 0 to 5% methanol in dichloromethane). MS: m/e=375.4 [M+H]$^+$.

Example 3

6-(3-Butyl-5-methyl-isoxazol-4-ylmethoxy)-pyridazine-3-carboxylic acid ((R)-2-hydroxy-1-methyl-ethyl)-amide

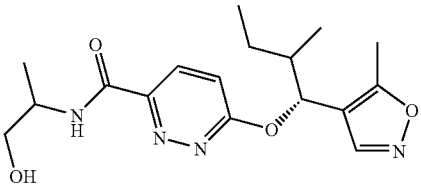 [SMILES: CCC(C)[C@@H](Oc1ccc(C(=O)NC(C)CO)nn1)c1cnoc1C]

As described for example 1e, 6-(3-butyl-5-methyl-isoxazol-4-ylmethoxy)-pyridazine-3-carboxylic acid methyl ester (100 mg, 0.33 mmol) was converted, using D-alaminol instead of isopropylamine, to the title compound (80 mg, 70%) which was obtained as a light brown oil after purification by chromatography (silica, 0 to 5% methanol in dichloromethane).

MS: m/e=349.4 [M+H]$^+$.

Example 4

6-(3-Butyl-5-methyl-isoxazol-4-ylmethoxy)-pyridazine-3-carboxylic acid (2-hydroxy-2-methyl-propyl)-amide

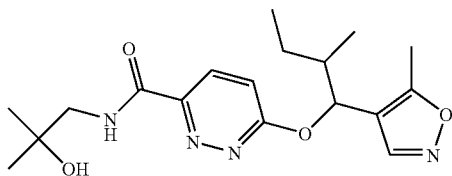 [SMILES: CCC(C)C(Oc1ccc(C(=O)NCC(C)(C)O)nn1)c1cnoc1C]

A mixture of 6-(3-butyl-5-methyl-isoxazol-4-ylmethoxy)-pyridazine-3-carboxylic acid methyl ester (110 mg, 0.36 mmol), 1-amino-2-methyl-propan-2-ol (39 mg, 0.43 mmol) and TBD (15 mg, 0.11 mmol) in toluene (0.5 mL) was stirred for 15 h at room temperature under argon. The reaction mixture was concentrated onto silica then purified by chromatography (silica, 0 to 5% methanol in dichloromethane) to afford the title compound (90 mg, 69%) as a colourless oil. MS: m/e=363.3 [M+H]$^+$.

Example 5

6-(3-Butyl-5-methyl-isoxazol-4-ylmethoxy)-pyridazine-3-carboxylic acid ((S)-2-hydroxy-1-methyl-ethyl)-amide

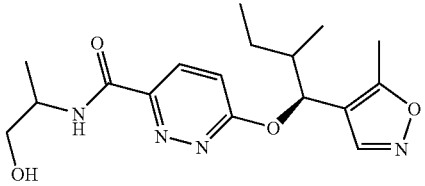 [SMILES: CCC(C)[C@H](Oc1ccc(C(=O)NC(C)CO)nn1)c1cnoc1C]

As described for example 4, 6-(3-butyl-5-methyl-isoxazol-4-ylmethoxy)-pyridazine-3-carboxylic acid methyl ester (100 mg, 0.33 mmol) was converted, using L-alaminol instead of 1-amino-2-methyl-propan-2-ol, to the title compound (60 mg, 53%) which was obtained as a light brown oil after purification by chromatography (silica, 0 to 5% methanol in dichloromethane).
MS: m/e=349.3 [M+H]$^+$.

Example 6

(S)-6-(3-Butyl-5-methyl-isoxazol-4-ylmethoxy)-pyridazine-3-carboxylic acid (tetrahydro-furan-3-yl)-amide

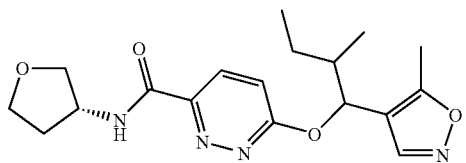 [SMILES: CCC(C)C(Oc1ccc(C(=O)N[C@@H]2CCOC2)nn1)c1cnoc1C]

As described for example 1e, 6-(3-butyl-5-methyl-isoxazol-4-ylmethoxy)-pyridazine-3-carboxylic acid methyl ester (110 mg, 0.36 mmol) was converted, using (S)-tetrahydrofuran-3-amine hydrochloride instead of isopropylamine, to the title compound (100 mg, 77%) which was obtained as a colourless oil after purification by chromatography (silica, 0 to 3.5% methanol in dichloromethane). MS: m/e=361.0 [M+H]$^+$.

Example 7

6-(3-Butyl-5-methyl-isoxazol-4-ylmethoxy)-pyridazine-3-carboxylic acid (2-hydroxy-1-methyl-ethyl)-amide

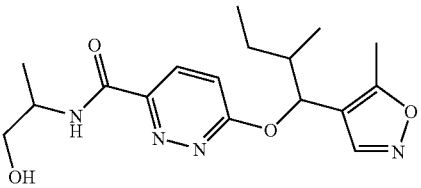 [SMILES: CCC(C)C(Oc1ccc(C(=O)NC(C)CO)nn1)c1cnoc1C]

As described for example 4, 6-(3-butyl-5-methyl-isoxazol-4-ylmethoxy)-pyridazine-3-carboxylic acid methyl ester (100 mg, 0.33 mmol) was converted, using rac-2-amino-1-propanol instead of 1-amino-2-methyl-propan-2-ol, to the title compound (105 mg, 84%) which was obtained as a light yellow oil after purification by chromatography (silica, 0 to 5% methanol in dichloromethane). MS: m/e=349.3 [M+H]$^+$.

Example 8

Rac-6-(3-Butyl-5-methyl-isoxazol-4-ylmethoxy)-pyridazine-3-carboxylic acid (tetrahydro-furan-3-yl)-amide

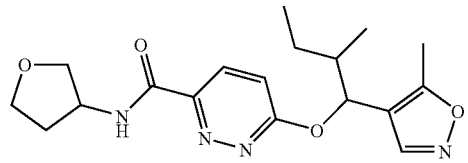 [SMILES: CCC(C)C(Oc1ccc(C(=O)NC2CCOC2)nn1)c1cnoc1C]

As described for example 1e, 6-(3-butyl-5-methyl-isoxazol-4-ylmethoxy)-pyridazine-3-carboxylic acid methyl ester (120 mg, 0.39 mmol) was converted, using rac-tetrahydrofuran-3-amine instead of isopropylamine, to the title compound (130 mg, 92%) which was obtained as a light yellow oil after purification by chromatography (silica, 0 to 5% methanol in dichloromethane). MS: m/e=361.5 [M+H]$^+$.

Example 9

6-(3-Butyl-5-methyl-isoxazol-4-ylmethoxy)-pyridazine-3-carboxylic acid amide

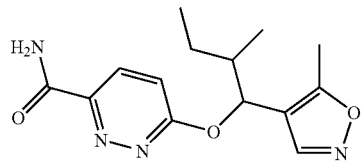 [SMILES: CCC(C)C(Oc1ccc(C(N)=O)nn1)c1cnoc1C]

a) 3-(3-Butyl-5-methyl-isoxazol-4-ylmethoxy)-6-chloro-pyridazine

To a stirred suspension of NaH (258 mg of a 55% dispersion in mineral oil) in THF (9 mL) at 0° C. under argon, was added a solution of (3-butyl-5-methyl-isoxazol-4-yl)-methanol (1.0 g, 5.9 mmol) in THF (18 mL) dropwise. The reaction mixture was warmed to room temperature. After 30 min the reaction mixture was cooled to 0° C. and a solution of 3,6-dichloropyridazine (908 mg, 6.1 mmol) in THF (18 mL) was added dropwise. After 16 h the reaction mixture was warmed to room temperature then quenched with water and extracted with ethyl acetate. The combined organic phases were dried, filtered and concentrated then purified by chromatography (silica, 10 to 60% ethyl acetate in heptane) to give the title compounds (1.31 g, 66%) as a light yellow liquid.

MS: m/e=282.2 [M+H]$^+$.

b) 6-(3-Butyl-5-methyl-isoxazol-4-ylmethoxy)-pyridazine-3-carboxylic acid ethyl ester A suspension of 3-(3-butyl-5-methyl-isoxazol-4-ylmethoxy)-6-chloro-pyridazine (1.2 g, 3.6 mmol) and sodium carbonate (379 mg, 3.6 mmol) in ethanol (20 mL) was evacuated and filled with argon five times. 1,1'-Bis(diphenylphosphino)ferrocene (198 mg, 3.6 mmol) and palladium(II) acetate (80 mg, 0.36 mmol) were added then the flask was evacuated again and filled with carbon monoxide. The reaction mixture was then heated to 50° C. After 15 h the reaction mixture was cooled, filtered through decalite and evaporated. The residue was purified by chromatography (silica, 0 to 50% ethyl acetate in heptane) to give the title compound (1.0 g, 88%) as a light yellow oil. MS: m/e=320.2 [M+H]$^+$.

c) 6-(3-Butyl-5-methyl-isoxazol-4-ylmethoxy)-pyridazine-3-carboxylic acid

To a solution of 6-(3-butyl-5-methyl-isoxazol-4-ylmethoxy)-pyridazine-3-carboxylic acid ethyl ester (960 mg, 3.0 mmol) in THF (10 mL) was added a solution of lithium hydroxide monohydrate (252 mg, 6.0 mmol) in water (10 mL) and the resulting mixture stirred at room temperature for 30 min. The mixture was acidified to pH 1 with HCl (1 N) and the resulting mixture extracted with ethyl acetate. The combined organic layers were then washed with water and brine, dried over sodium sulfate and evaporated to afford the title compound (850 mg, 87%) which was obtained as a red gum. MS: m/e=290.1 [M−H]$^-$.

d) 6-(3-Butyl-5-methyl-isoxazol-4-ylmethoxy)-pyridazine-3-carboxylic acid amide To a solution of 6-(3-butyl-5-methyl-isoxazol-4-ylmethoxy)-pyridazine-3-carboxylic acid (100 mg, 0.31 mmol) in DMF (5 mL) was added 1,1'-carbonyldiimidazole (60 mg, 0.37 mmol). The resulting reaction mixture was stirred for 1 h at 60° C. and then treated with an ammonium hydroxide solution (476 µL, 3.1 mmol). After 2 h the reaction mixture was evaporated and purification by chromatography (silica, 0 to 100% ethyl acetate in heptane) afforded the title compound (49 mg, 55%) as an off white solid. MS: m/e=313.2 [M+Na]$^+$.

The invention claimed is:
1. A compound of formula I,

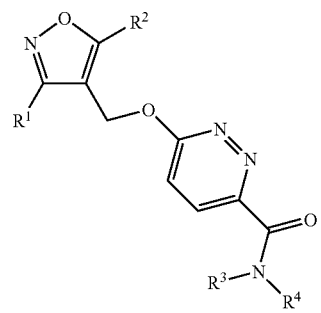

wherein
- $R^1$ is lower alkyl or lower alkyl substituted by 1-5 substituents individually selected from amino, halogen, (lower alkyl, lower alkyl)N—— and (lower alkyl, H)N——;
- $R^2$ is H, lower alkyl or lower alkyl substituted by 1-5 substituents individually selected from amino, halogen, halogen-lower alkoxy, hydroxy, lower alkoxy, (lower alkyl, lower alkyl)N——, (lower alkyl, H)N——, nitro and lower alkyl-S(O)$_2$——;
- $R^3$ is H, lower alkyl or lower alkyl substituted by 1-5 substituents individually selected from amino, halogen, halogen-lower alkoxy, hydroxy, lower alkoxy, (lower alkyl, lower alkyl)N——, (lower alkyl, H)N——, nitro and lower alkyl-S(O)$_2$——;
- $R^4$ is selected from the group consisting of
  - i) H,
  - ii) lower alkyl,
  - iii) lower alkyl substituted by 1-5 substituents individually selected from amino, halogen, halogen-lower alkoxy, hydroxy, lower alkoxy, (lower alkyl, lower alkyl)N——, (lower alkyl, H)N——, nitro and lower alkyl-S(O)$_2$——;
  - iv) heterocyclyl, and
  - v) heterocyclyl substituted by 1-4 substituents individually selected from amino, halogen, halogen-lower alkoxy, halogen-lower alkyl, hydroxy, hydroxy-lower alkyl, lower alkoxy, lower alkoxy-lower alkyl, lower alkyl, (lower alkyl, lower alkyl)N——, (lower alkyl, H)N——, nitro and lower alkyl-S(O)$_2$——;

or a pharmaceutically acceptable salt or ester thereof.

2. The compound of claim 1, wherein $R^1$ is lower alkyl.
3. The compound of claim 2, wherein $R^1$ is n-butyl.
4. The compound of claim 1, wherein $R^2$ is lower alkyl.
5. The compound of claim 4, wherein $R^2$ is methyl.
6. The compound of claim 1, wherein $R^3$ is H.
7. The compound of claim 1, wherein $R^4$ is selected from
  - i) H,
  - ii) lower alkyl,
  - iii) lower alkyl substituted by 1-2 hydroxy groups, and
  - iv) heterocyclyl.
8. Compound of claim 7, wherein $R^4$ is selected from
  - i) lower alkyl,
  - ii) lower alkyl substituted by 1-2 hydroxy groups, and
  - iii) heterocyclyl.
9. The compound of claim 8, wherein $R^4$ is isopropyl, tetrahydrofuranyl, 2-hydroxy-1-methyl-ethyl or 2-hydroxy-2-methyl-propyl.
10. The compound of claim 1 individually selected from the group consisting of 6-(3-Butyl-5-methyl-isoxazol-4-ylmethoxy)-pyridazine-3-carboxylic acid isopropylamide, 6-(3-Butyl-5-methyl-isoxazol-4-ylmethoxy)-pyridazine-3-carboxylic acid (tetrahydro-pyran-4-yl)-amide, 6-(3-Butyl-5-methyl-isoxazol-4-ylmethoxy)-pyridazine-3-carboxylic acid ((R)-2-hydroxy-1-methyl-ethyl)-amide, 6-(3-Butyl-5-methyl-isoxazol-4-ylmethoxy)-pyridazine-3-carboxylic acid (2-hydroxy-2-methyl-propyl)-amide, 6-(3-Butyl-5-methyl-isoxazol-4-ylmethoxy)-pyridazine-3-carboxylic acid ((S)-2-hydroxy-1-methyl-ethyl)-amide, (S)-6-(3-Butyl-5-methyl-isoxazol-4-ylmethoxy)-pyridazine-3-carboxylic acid (tetrahydro-furan-3-yl)-amide, 6-(3-Butyl-5-methyl-isoxazol-4-ylmethoxy)-pyridazine-3-carboxylic acid (2-hydroxy-1-methyl-ethyl)-amide, 6-(3-Butyl-5-methyl-isoxazol-4-ylmethoxy)-pyridazine-3-carboxylic acid (tetrahydro-furan-3-yl)-amide, and 6-(3-Butyl-5-methyl-isoxazol-4-ylmethoxy)-pyridazine-3-carboxylic acid amide, or a pharmaceutically acceptable salt or ester thereof.

11. The compound of claim 1 individually selected from the group consisting of (S)-6-(3-Butyl-5-methyl-isoxazol-4-ylmethoxy)-pyridazine-3-carboxylic acid (tetrahydro-furan-3-yl)-amide, 6-(3-Butyl-5-methyl-isoxazol-4-ylmethoxy)-pyridazine-3-carboxylic acid isopropylamide, 6-(3-Butyl-5-methyl-isoxazol-4-ylmethoxy)-pyridazine-3-carboxylic acid ((R)-2-hydroxy-1-methyl-ethyl)-amide, 6-(3-Butyl-5-methyl-isoxazol-4-ylmethoxy)-pyridazine-3-carboxylic acid ((S)-2-hydroxy-1-methyl-ethyl)-amide, and 6-(3-Butyl-5-methyl-isoxazol-4-ylmethoxy)-pyridazine-3-carboxylic acid (2-hydroxy-1-methyl-ethyl)-amide, or a pharmaceutically acceptable salt or ester thereof.

12. The compound of claim 1 which is (S)-6-(3-Butyl-5-methyl-isoxazol-4-ylmethoxy)-pyridazine-3-carboxylic acid (tetrahydro-furan-3-yl)-amide, or a pharmaceutically acceptable salt or ester thereof.

13. A pharmaceutical composition comprising a therapeutically effective amount of a compound of formula I

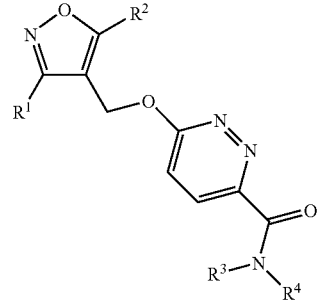

wherein
   $R^1$ is lower alkyl or lower alkyl substituted by 1-5 substituents individually selected from amino, halogen, (lower alkyl, lower alkyl)N— and (lower alkyl, H)N—;
   $R^2$ is H, lower alkyl or lower alkyl substituted by 1-5 substituents individually selected from amino, halogen, halogen-lower alkoxy, hydroxy, lower alkoxy, (lower alkyl, lower alkyl)N—, (lower alkyl, H)N—, nitro and lower alkyl-$S(O)_2$—;
   $R^3$ is H, lower alkyl or lower alkyl substituted by 1-5 substituents individually selected from amino, halogen, halogen-lower alkoxy, hydroxy, lower alkoxy, (lower alkyl, lower alkyl)N—, (lower alkyl, H)N—, nitro and lower alkyl-$S(O)_2$—;
   $R^4$ is selected from the group consisting of
   i) H,
   ii) lower alkyl,
   iii) lower alkyl substituted by 1-5 substituents individually selected from amino, halogen, halogen-lower alkoxy, hydroxy, lower alkoxy, (lower alkyl, lower alkyl)N—, (lower alkyl, H)N—, nitro and lower alkyl-$S(O)_2$—;
   iv) heterocyclyl, and
   v) heterocyclyl substituted by 1-4 substituents individually selected from amino, halogen, halogen-lower alkoxy, halogen-lower alkyl, hydroxy, hydroxy-lower alkyl, lower alkoxy, lower alkoxy-lower alkyl, lower alkyl, (lower alkyl, lower alkyl)N—, (lower alkyl, H)N—, nitro and lower alkyl-$S(O)_2$—;
or a pharmaceutically acceptable salt or ester thereof and a pharmaceutically acceptable carrier.

* * * * *